United States Patent
Scarlin et al.

(10) Patent No.: US 8,359,925 B2
(45) Date of Patent: Jan. 29, 2013

(54) ROTOR DISK WELD INSPECTION METHOD AND ARRANGEMENT

(75) Inventors: Richard Brendon Scarlin, Oberflachs (CH); Andreas Pirscher, Nussbaumen (CH); Maurus Herzog, Schinznach Dorf (CH)

(73) Assignee: Alstom Technology Ltd., Baden (CH)

( * ) Notice: Subject to any disclaimer, the term of this patent is extended or adjusted under 35 U.S.C. 154(b) by 681 days.

(21) Appl. No.: 12/588,026

(22) Filed: Oct. 1, 2009

(65) Prior Publication Data

US 2010/0089165 A1    Apr. 15, 2010

(30) Foreign Application Priority Data

Oct. 1, 2008    (EP) .................................... 08105469

(51) Int. Cl.
    *G01N 29/26*    (2006.01)
(52) U.S. Cl. ............................................ 73/629; 416/61
(58) Field of Classification Search .................... 73/622, 73/623, 629; 416/61
    See application file for complete search history.

(56) References Cited

U.S. PATENT DOCUMENTS

| | | | |
|---|---|---|---|
| 3,929,005 A * | 12/1975 | Parkinson et al. | 73/622 |
| 4,194,400 A * | 3/1980 | Staff | 73/623 |
| 6,128,820 A | 10/2000 | Nolan et al. | |
| 6,152,697 A | 11/2000 | Konishi et al. | |
| 6,354,152 B1 | 3/2002 | Herlik | |
| 6,494,683 B1 | 12/2002 | Nolan et al. | |

FOREIGN PATENT DOCUMENTS

| | | |
|---|---|---|
| EP | 0 964 135 A2 | 12/1999 |
| WO | WO 2005/119228 A1 | 12/2005 |

OTHER PUBLICATIONS

European Search Report dated Apr. 7, 2009.

* cited by examiner

*Primary Examiner* — John Chapman, Jr.
(74) *Attorney, Agent, or Firm* — Buchanan Ingersoll & Rooney, P.C.

(57) ABSTRACT

A method is disclosed for inspecting a weld joining a first rotor disk made of nickel alloy and having an inner surface and an outer surface concentric with the rotor's longitudinal axis to a second rotor disk having an inner surface and an outer surface concentric with the rotor's longitudinal axis. The weld made of nickel alloy fills a radial gap between the rotor disks, and has a dissimilar microstructure to either of the rotor disks. The method includes forming at least one slot in the first rotor disk extending through either the inner surface or the outer surface of the first rotor disk terminating in the first rotor disk; and passing an inspection signal from the first slot to the weld to inspect the weld for defects.

17 Claims, 4 Drawing Sheets

# ROTOR DISK WELD INSPECTION METHOD AND ARRANGEMENT

RELATED APPLICATION

This application claims priority under 35 U.S.C. §119 to European Patent Application No. 08105469.4 filed in Europe on Oct. 1, 2008, the entire content of which is hereby incorporated by reference in its entirety.

FIELD

The disclosure relates to weld inspection methods and suitable arrangements.

BACKGROUND INFORMATION

Rotors, particularly in larger turbo machines, are formed by welding together a plurality of disks. Because of axial temperature gradients experienced during operation of these machines, the disks can be made of different materials at different locations along the rotor axis. For example, in the highest temperature segment of a rotor, where high creep strength is desired, a nickel alloy having a face-centred cubic atomic structure and a high proportion of chromium can be used. Other alloying elements, such as for example molybdenum, tungsten and vanadium, can be used to additionally increase the creep strength. The rotor in this region therefore can include a plurality of nickel alloy disks welded together by a weld made of nickel alloy.

In the low temperature segment where lower cost material with a high yield strength and toughness may be used, the rotor may be made of ferritic-martensitic steel with a body-centred cubic atomic structure. The rotor in this region therefore can include a plurality of steel disks welded together by a weld made of steel.

At the interface barrier between the high and lower temperature regions welds of nickel alloy may be used to weld disks of nickel alloy and steel together.

Particularly in the case of rotors of large steam or gas turbines, the quality of the weld seams between the individual rotor disks can be important to ensuring the mechanical integrity of the rotor. It can therefore be very desirable for the weld to be inspected for defects as accurately as possible and with as high a resolution as possible, using non-destructive inspection methods such as ultrasonic or isotope inspection. This may involve the passing of an inspection signal through an outer surface of the rotor angled towards or through the joining weld.

Ultrasound inspection methods can have significant advantages as compared to isotope methods. However, attenuation of the ultrasonic inspection signal can reduce the resolution of the inspection method, particularly at inspection points of the weld distant from the inspection signal source, rendering the inspection method ineffective. There are a number of causes of attenuation. One cause is high attenuation in some materials, nickel alloys for example. Reflection and refraction is another cause and is most evident when the ultrasonic wave passes through two materials with different atomic structure for example from steel, which has a low attenuation property, across into a weld made of nickel alloy. Further attenuation, although not to the same extent as across atomic structure boundaries, can occur across microstructure interfaces, such as between a nickel alloy disk and nickel weld.

During disk manufacture, to ensure optimum mechanical properties the disk undergoes numerous heat treatment and preparation steps. In contrast, the weld, while it may have the same material composition as that of the disk, does not undergo the same heat treatment steps. As a result a pseudo forged—cast boundary and resulting microstructure difference is created between the disk and weld where weld metal displays the properties of "casting" while the disk the properties of "forging". As an ultrasonic inspection signal passes from a nickel alloy disk through to a nickel weld, attenuation occurs at the disk/weld microstructure interface.

While inspection methods utilising isotope radiation do not suffer from the same attenuation and reflection/refraction problems of inspection methods utilising ultrasonic waves, it is known to only deviate the angle of the isotope radiation no more than a few degrees from the radial centreline of the weld being inspected. As a result isotope inspection methods are limited in their ability of determine the size and depth of any defects. As the normal process of repairing a defective weld is to remove portions of the weld only up to the defect, imprecise location of the defect necessitates removing more weld than is necessary.

SUMMARY

A method is disclosed for inspecting a weld joining a first rotor disk made of nickel alloy and having an inner surface and an outer surface concentric with a rotor's longitudinal axis to a second rotor disk having an inner surface and an outer surface concentric with the rotor's longitudinal axis, wherein the weld, made of nickel alloy, fills a radial gap between said first and second rotor disks and has a dissimilar microstructure to either of said first and second rotor disks, the method comprising: a) forming at least a first slot in the first rotor disk part way through the first rotor disk from either said inner surface or said outer surface of said first rotor disk; and b) passing an inspection signal from said first slot to said weld to inspect said weld for defects.

A turbine rotor is disclosed comprising: a first rotor disk having an inner surface and an outer surface concentric with a rotor's longitudinal axis; a second rotor disk having an inner surface and an outer surface concentric with the rotor's longitudinal axis; a weld filling a radial gap between said first and second rotor disks and having a dissimilar microstructure to said first and second rotor disks, and a radial depth; and at least one slot, extending part way into at least one of the first and second disks from any one of said inner and outer surface and configured to receive an inspection signal source, wherein a distance of the slot to a weld radial midpoint is less than a distance between any one of said surfaces and the weld radial midpoint.

An improved inspection method for detecting defects in welds joining rotor disks is disclosed.

Exemplary embodiments can minimize the distance an inspection signal passes in order to inspect the full length of a weld by providing slots in the rotor disk in which an inspection signal source can be received.

A method is disclosed for inspecting a weld joining a first rotor disk, made of nickel alloy and having an inner surface and an outer surface concentric with the rotor's longitudinal axis, to a second rotor disk having an inner surface and an outer surface concentric with the rotor's longitudinal axis. The weld, made of nickel alloy, fills a radial gap between the first and second rotor disks and has a dissimilar microstructure to either of the first and second rotor disks. The method can include:

a) forming at least one slot in the first rotor disk part way through the first rotor disk from either the inner surface or the outer surface of the first rotor disk; and b) passing an inspection signal from the first slot to the weld to inspect the weld for defects.

The slots can allow the reduction of the inspection signal flow path length compared to methods where the inspection signal originates from external surfaces of the rotor. When the inspection signal is an ultrasonic inspection device, the effect of inspection signal attenuation caused by the nickel alloy of the disk coupled with microstructure interface reflection/refraction at the weld—disk boundary, can be mitigated.

For isotope radiation applications the isotope source can be located in a slot of one disk while isotope film is located either in a slot of another disk or alternatively on the surface of the other disk. In this arrangement, radiation passes across at least part of the weld as it passes from the isotope source to the isotope film, enabling cross referencing of the defects and enabling improved ability to located defects as compared to inspections made through the radial depth of the weld with no axial directional component. In addition the need to access both radial ends of the weld is avoided. In this way the need to locate the isotope source at one weld end and the isotope film at the other weld end can be avoided. This can be advantageous as it is often not possible to access the inside end of a weld.

Following the inspection of the weld metal, the slots can be incorporated into other features of the rotor disks such as mounting channels for turbine blade roots. In this case the slots, after inspection of the joining weld, may only be partially filled with weld filler to restore rotor partial thickness otherwise the slots may be fully refilled. In this way, the desired metal thickness and strength of the rotor disk can be restored after inspection so that its in-service performance is not compromised by the slot formation.

If the depth of the slot is too great, the mechanical strength of the rotor disk can be compromised such that the integrity of weld filler used to refill the slot can be used to perform a structural function. In this case the refill would have itself to be inspected. To avoid an additional inspection step, exemplary embodiments can provide that the or each slot extends through no more than one half of the radial disk section depth into which the slot is formed.

Another aspect includes the forming of a plurality of slots into the first rotor disk, the second rotor disk or both the first and second rotor disks. Such an arrangement enables increased slot depth before mechanical integrity concerns are raised. In an exemplary embodiment, the plurality of slots can be in the form of holes.

Further embodiments of the disclosure provide a turbine rotor having a first rotor disk, including an inner surface and an outer surface concentric with the rotor's longitudinal axis, a second rotor disk having an inner surface and an outer surface concentric with the rotor's longitudinal axis, and a weld filling a radial gap between said rotor disks and having a dissimilar microstructure to the rotor disks. The turbine rotor can include at least one slot, configured to receive an inspection signal source, extending partly through the disk from outer or inner surface of the rotor disk and terminating in that disk, wherein the distance between the weld radial mid point and the slot is less than the distance between the weld radial mid point and any of the rotor surfaces. This can enable reduced weld inspection signal path length so by ameliorating the problem of signal attenuation.

BRIEF DESCRIPTION OF THE DRAWINGS

Other objectives and advantages of the present disclosure will become apparent from the following description, taken in connection with the accompanying drawing.

By way of example, embodiments are described more fully hereinafter with reference to the accompanying drawings, in which.

DETAILED DESCRIPTION

Figure 1:
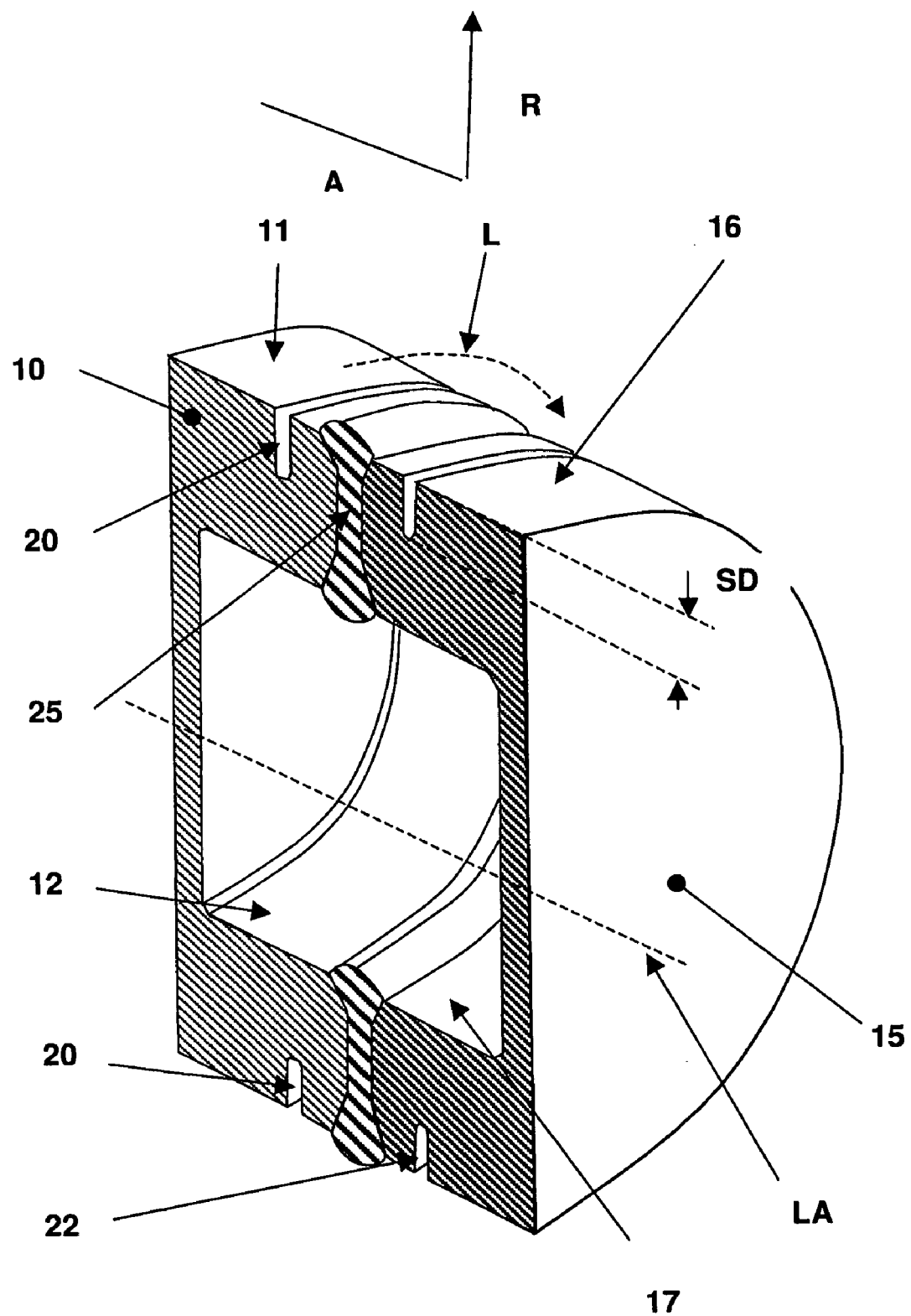
FIG. 1 is a sectional view of two welded rotor disks showing rotor disks with slots according to an embodiment of the disclosure.

Exemplary embodiments of the present disclosure are now described with reference to the drawings, wherein like reference numerals are used to refer to like elements. For purposes of explanation, numerous specific details are set forth in order to provide a thorough understanding of the disclosure. It may be evident, however, that the disclosure may be practiced without these specific details.

FIG. 1 shows a first rotor disk 10 welded to a second rotor disk 15 wherein the weld 25 fills a radial gap between the two rotor disks 10,15. The first rotor disk 10 and the weld 25 are both made of nickel alloy however, due to their different thermal treatment during manufacturing, they have different microstructures. The first rotor disk 10 has a microstructure created typically by forging while the weld 25 has one created typically by casting. While FIG. 1 further shows rotor disks 10,15 having dissimilar atomic structures, for example when the first rotor disk 10 is made of nickel alloy and has a face centered atomic structure and the second rotor disk 15 is made of steel alloy and has a body centred atomic structure, both disks 10,15 may be constructed of a nickel alloy.

The first rotor disk 10 has an inner 12 and an outer surface 11 that are concentric with the longitudinal axis of the rotor LA. In the embodiment shown in FIG. 1 a slot 20 is formed in the first rotor disk 10 extending from the outer surface 11 into the rotor disk 10 and terminating in the rotor disk 10 so as to extend only part way through the depth of the rotor disk 10. The slot 20 further extends circumferentially around the rotor disk 10. The slot 20 may however also extend from the inner surface 12 or alternative in both the inner 12 and outer 11 surfaces of the first rotor disk 10 all the while not extending through the complete depth of the rotor disk 10 that is, it only extends part was into the rotor disk 10.

The second rotor disk 15 also has an inner surface 17 and an outer 16 surface that is concentric with the longitudinal axis of rotor LA. In the embodiment shown in FIG. 1 a slot 22 is formed in the second rotor disk 15 extending from the outer surface 16 into the rotor disk 15 and terminating in the rotor disk 15 so as to extend only partially through the depth of the disk 15. The slot 22 further extends circumferentially around the rotor disk 15. The slot 22 may however also be formed in the inner surface 17 or alternatively in both the inner surface 17 and outer 16 surface of the second rotor disk 15 all the while not extending through the complete depth of the rotor disk 15.

A weld 25 joins the first 10 and second 15 rotor disks by filling and spanning a radial gap between the two rotor disks 10,15 and is made of nickel alloy similar to the disk 10,15 with the highest temperature class.

When the weld 25 is made of nickel alloy and inspected by means of ultrasound and the slot 20 and the two rotor disks 10,15 are made of nickel alloy and steel respectively the slot 20 is formed preferably only in the first rotor disk 10. In this arrangement the ultrasonic waves 32 do not experience the level of attenuation that would occur if the slot 22 was formed in the second rotor disk 15 and the ultrasonic waves 32 were required to cross the atomic structure boundary formed between the steel of the second rotor disk 15 and the nickel alloy of the weld 25.

Figure 2:
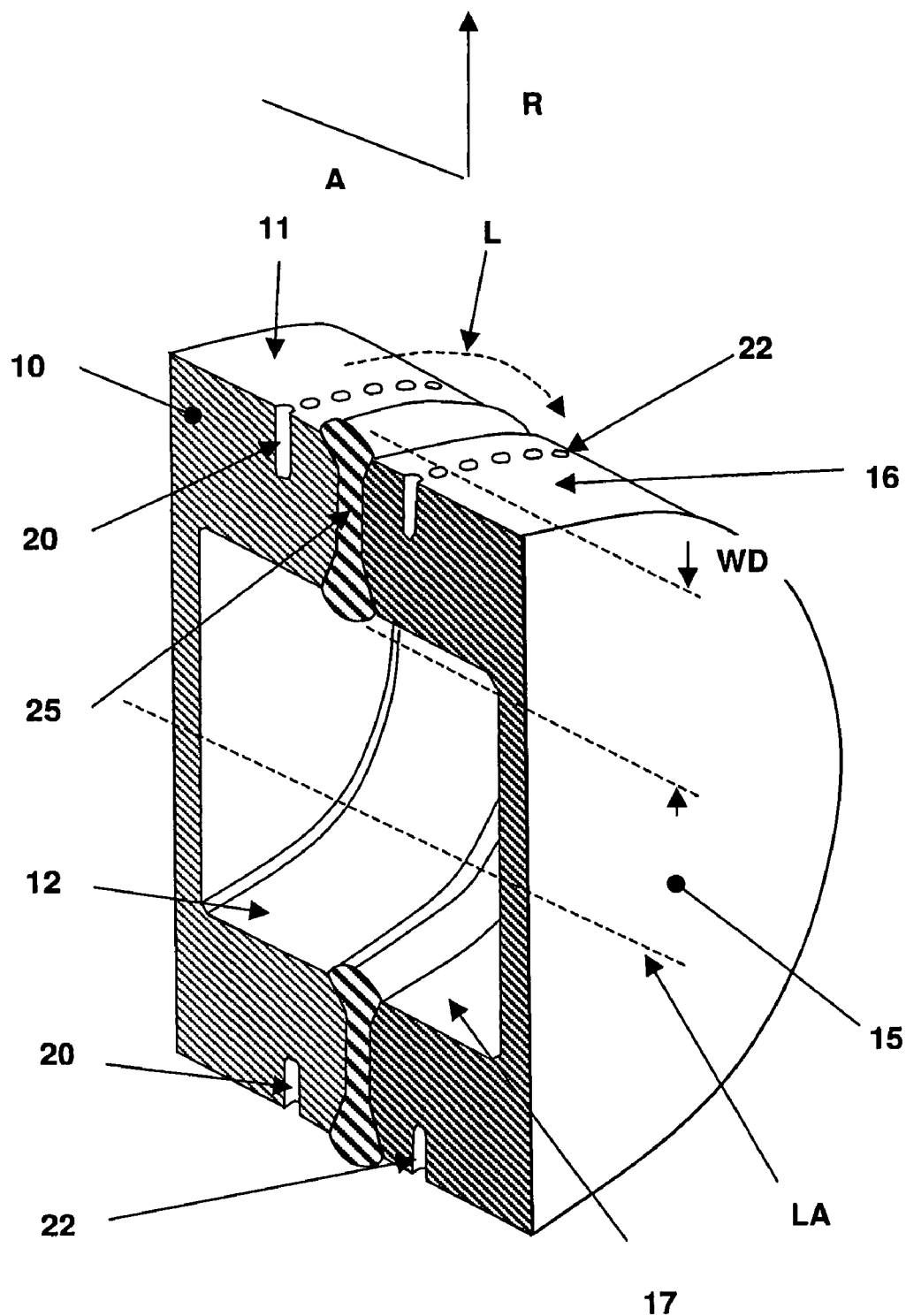
FIG. 2 is a sectional view of two welded rotor disks showing rotor disks with a plurality of slots according to an embodiment of the disclosure.

FIG. 2 shows the two rotor disks 10,15 of FIG. 1 welded together. It further shows slots 20,22 formed in the rotor disks according to another embodiment. The slots 20,22 formed in the outer surfaces 11, 16 of the first 10 and second 15 rotor disks comprise a plurality of holes extending from the outer surfaces 11, 16 of the rotor disks 10,15 into the rotor disks 10, 15 distributed circumferentially around the rotor disks 10,15. While the slots 20,22 are shown extending from outer surfaces 11,16 of the rotor disks 10, 15 the plurality of slots 20,22 may also be formed in the inner surfaces 12, 17 or alternative in both the inner 12, 17 and outer 11, 16 surfaces of the rotor disks 10, 15 all the while not extending through the complete depth of the rotor disks 10,15.

Depending on the requirements of the inspection method used to detect weld defects 27 the slots 20 in the form of holes may be formed only in one of the rotor disks 10, 15. This is the case, for example, when the inspection device is an ultrasonic inspection device 30 that incorporates both a source and a detector.

Figure 3:
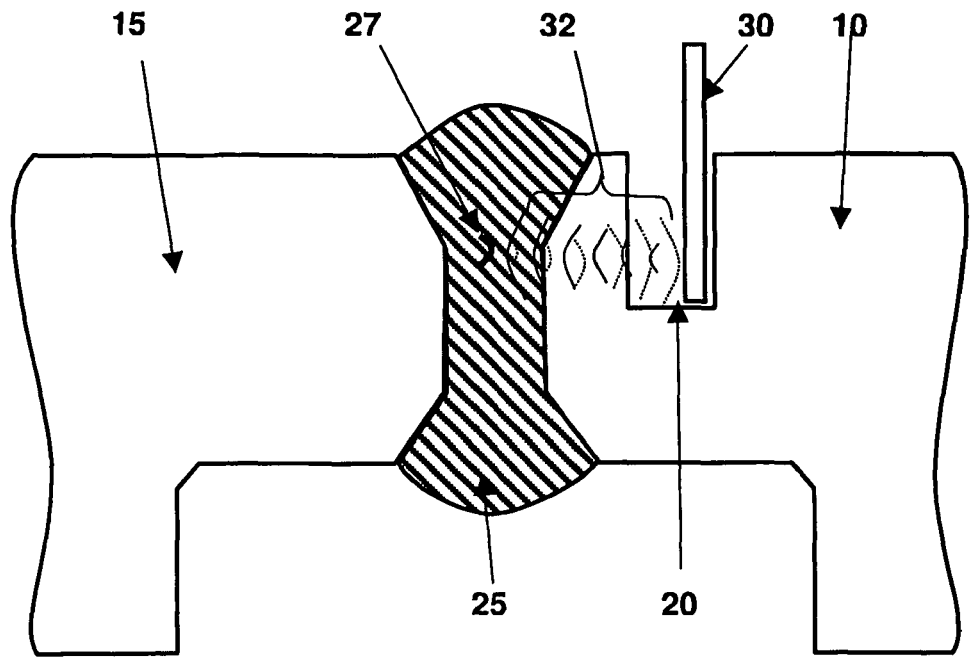
FIG. 3 is an expanded view of the rotor disk of FIG. 1 or FIG. 2 showing a weld being inspected by ultrasonic waves.

FIG. 3 shows an ultrasonic inspection device 30 inserted into a slot in the first rotor disk 20 of an embodiment of the disclosure. The ultrasonic waves 32 emitted from the ultrasonic inspection device 30 are transmitted from the slot 20 to the weld 25. The ultrasonic inspection device 30, by means of reflection of ultrasonic waves 32 across the radial weld depth WD, detects weld defects 27.

Figure 4:
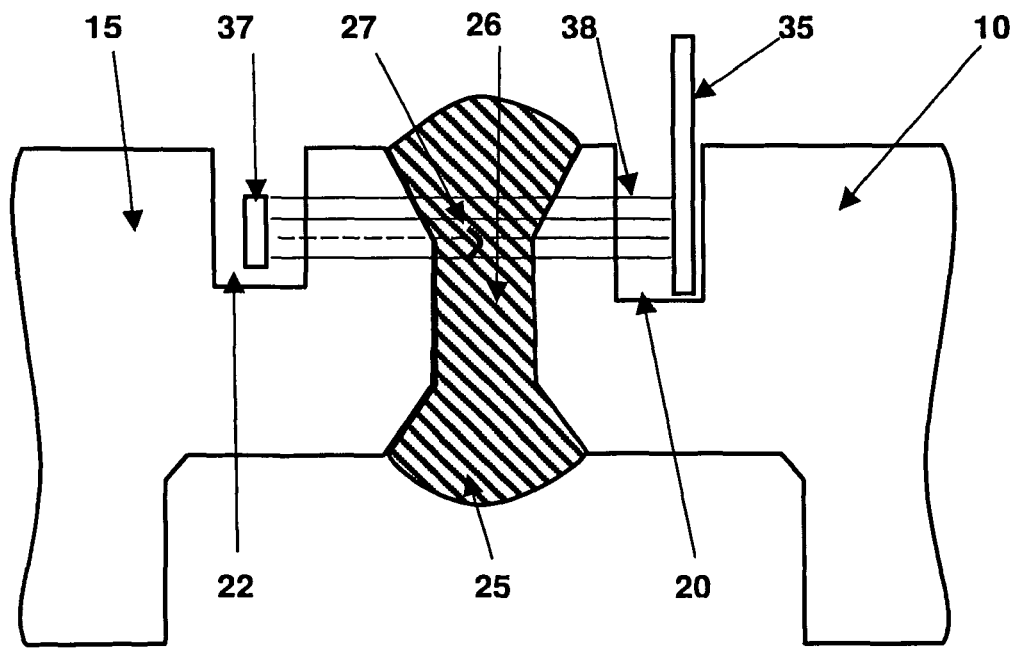
FIG. 4 is an expanded view of the rotor disk of FIG. 1 or FIG. 2 the weld being inspected by isotope radiation.

FIG. 4 shows an isotope source 35 inserted into a slot 20 of a first rotor disk 10 and isotope film 37 inserted in a slot 22 of a second rotor disk 15. Shown further is the inspection of the weld 25 for defects 27 by the emission of isotope radiation 38 from the isotope source 35 through the weld 25 to isotope film 37 inserted in a slot 22 of the second disk 15.

Figure 5:
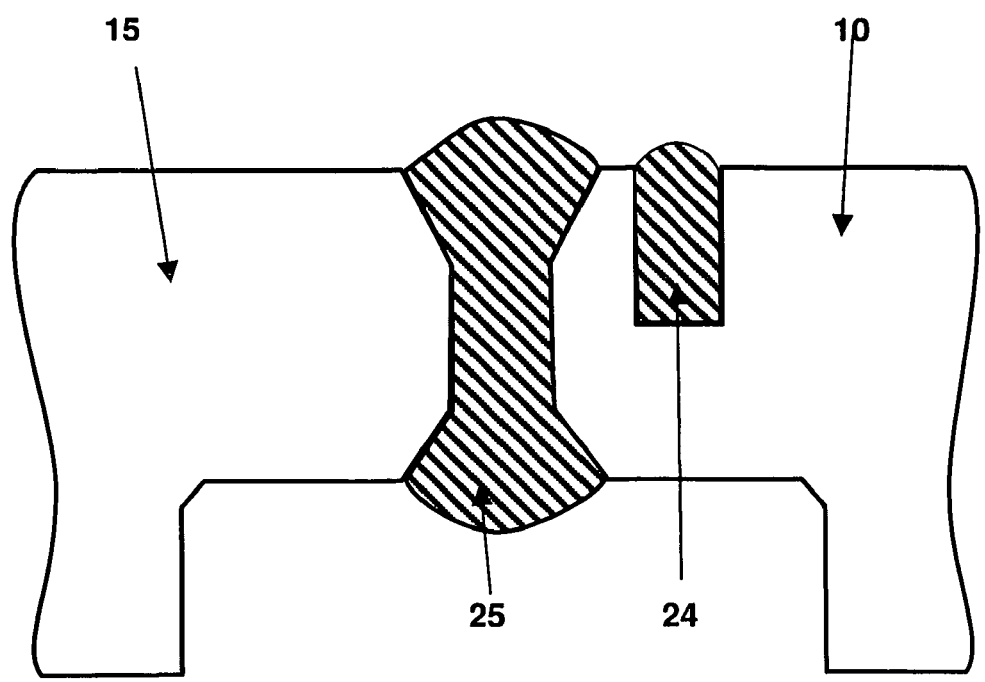
FIG. 5 is an expanded view of a rotor disk with slots according to an embodiment of the disclosure showing a filled weld.

FIG. 5 shows a filled slot 24, filled following inspection of the weld 25.

In each of the exemplified embodiments the depth of the slot SD is preferably no more than half the depth of radial depth of the rotor disk 10, 15 through the section at which the slot 20, 22 is made. This ensures that the slots 20,22 do not have a major material effect on the integrity of the disks 10,15. Further while preferably the slots 20, 22 are located proximal to the weld 25 so as to minimize attenuation of the inspection signal they are not to be located so close to the weld 25 that they could interfere with weld integrity. In an exemplary embodiment this is achieved by the distance between the weld radial mid point 26 and the slot 20,22 being less than the distance between the weld radial mid point 26 and any of the rotor surfaces. This enables reduced weld inspection signal path length so by ameliorating the problem of signal attenuation Yet further the slots 20, 22 may also take any suitable form including cavities, holes and grooves and in all cases are configured so as to be able to receive a inspection signal source, such as an isotope source 35 or ultrasonic inspection device 30 and/or inspection signal film such as isotope film 37.

Although the disclosure has been herein shown and described in what is considered to be a practical, exemplary embodiment, it is recognized that departures can be made within the scope of the disclosure, which is not to be limited to details described herein but is to be accorded the full scope of the appended claims so as to embrace any and all equivalent devices and apparatus. For example, while exemplary embodiments are particularly applicable to steam turbines because they have relatively thick rotors, exemplary features disclosed herein can also be applied to rotors of other machines, for example gas turbines.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

REFERENCE NUMBERS

10 First rotor disk
11 Outer surface of first rotor disk
12 Inner surface of first rotor disk
15 Second rotor disk
16 Outer surface of second rotor disk
17 Inner surface of rotor disks
20 Slot in first rotor disk
22 Slot in second rotor disk
24 Filled slot
25 Weld with weld filler joining the rotor disks
26 Weld radial midpoint
27 Weld defect
30 Ultrasonic inspection device
32 Ultrasonic waves
35 Isotope source
37 Isotope film
38 Isotope radiation
A Axial direction
R Radial direction
L Weld length
LA Rotor and rotor disks longitudinal axis
SD Slot depth
WD Radial weld depth

What is claimed is:

1. A method for inspecting a weld joining a first rotor disk made of nickel alloy and having an inner surface and an outer surface concentric with a rotor's longitudinal axis to a second rotor disk having an inner surface and an outer surface concentric with the rotor's longitudinal axis, wherein the weld, made of nickel alloy, fills a radial gap between said first and second rotor disks and has a dissimilar microstructure to either of said first and second rotor disks, the method comprising:
   a) forming at least a first slot in the first rotor disk part way through the first rotor disk from either said inner surface or said outer surface of said first rotor disk; and
   b) passing an inspection signal from said first slot to said weld to inspect said weld for defects,
   wherein the first slot extends no more than one half of a radial weld depth.

2. The method of claim 1, wherein atomic structures of said first rotor disk and said second rotor disk are dissimilar.

3. The method of claim 2, wherein the forming includes:
   forming at least one slot in the second rotor disk extending part way through the second rotor disk through either said inner surface or said outer surface of said second rotor disk.

4. The method of claim 3, wherein a plurality of slots are formed into said first rotor disk, said second rotor disk or both the first and second rotor disks.

5. The method of claim 4, including, after the passing, of at least partially refilling of the first slot with weld filler.

6. The method of claim 4, wherein said inspection signal is an ultrasonic sound wave.

7. The method of claim 4, wherein the first rotor disk has a face centered atomic structure.

8. The method of claim 4, wherein said first and second rotor disks are steam turbine rotor disks.

9. The method of claim 1, wherein the forming includes:
forming at least one slot in the second rotor disk extending part way through the second rotor disk through either said inner surface or said outer surface of said second rotor disk.

10. The method of claim 1, wherein a plurality of slots are formed into said first rotor disk, said second rotor disk or both the first and second rotor disks.

11. The method of claim 1, including, after the passing, at least partially refilling of the first slot with weld filler.

12. The method of claim 1, wherein said inspection signal is an ultrasonic sound wave.

13. The method of claim 1, wherein the first rotor disk has a face centered atomic structure.

14. The method of claim 13, wherein the second rotor disk has a body centered atomic structure.

15. The method of claim 1, wherein the second rotor disk has a body centered atomic structure.

16. The method of claim 1, wherein said first and second rotor disks are steam turbine rotor disks.

17. A turbine rotor comprising:
a first rotor disk having an inner surface and an outer surface concentric with a rotor's longitudinal axis;
a second rotor disk having an inner surface and an outer surface concentric with the rotor's longitudinal axis;
a weld filling a radial gap between said first and second rotor disks and having a dissimilar microstructure to said first and second rotor disks, and a radial depth; and
at least one slot, extending part way into at least one of the first and second disks from any one of said inner or outer surface and configured to receive an inspection signal source, wherein a distance of the slot to a weld radial midpoint is less than a distance between any one of said surfaces and the weld radial midpoint.

* * * * *